United States Patent [19]

Janssen

[11] Patent Number: 4,584,866
[45] Date of Patent: Apr. 29, 1986

[54] METHOD AND APPARATUS FOR THE DETERMINATION OF NON-DISSOLVED GAS IN LIQUIDS

[75] Inventor: Wladmir Janssen, Montreal, Canada

[73] Assignee: Domtar, Inc., Montreal, Canada

[21] Appl. No.: 675,002

[22] Filed: Nov. 26, 1984

[51] Int. Cl.$^4$ .............................................. G01N 7/14
[52] U.S. Cl. ............................................ 73/19; 73/63
[58] Field of Search ............... 73/19, 63, 32 R, 32 A; 162/198, 263

[56] References Cited

U.S. PATENT DOCUMENTS

| | | | |
|---|---|---|---|
| 3,060,722 | 10/1962 | Migdal et al. | 73/19 |
| 3,673,853 | 7/1972 | Griswold et al. | 73/19 |
| 4,201,082 | 5/1980 | Dockhorn et al. | 73/19 |

FOREIGN PATENT DOCUMENTS 46408  11/1962  Poland .................................... 73/19

Primary Examiner—Stephen A. Kreitman

[57] ABSTRACT

The method enabling the quick determination of non-dissolved or free gas in a liquid sample. Involves measuring the density of a liquid sample in a closed vessel, subjecting this sample to a reduced pressure and thereby expanding the "free" gas in the liquid sample. After this expansion has taken place, but before allowing dissolved gas to come out of solution, the volume is fixed and a second density measurement is taken. An apparatus therefor is also disclosed. The apparatus comprises: a chamber wherein a liquid sample is subjected to a reduced pressure and an increased volume, and a means for density measurements of the said liquid sample. Also disclosed are means to transfer into the chamber a liquid sample while avoiding the entrapment of gas bubbles. Preferably the chamber has a flexible wall coupled to a suspended weight to enable quick expansion of the chamber while minimizing friction losses and liquid leakage. Once the "free" gas has expanded, the volume is fixed and a density measurement is taken.

18 Claims, 3 Drawing Figures

METHOD AND APPARATUS FOR THE DETERMINATION OF NON-DISSOLVED GAS IN LIQUIDS

This invention is directed toward an improved method and apparatus for use in measuring the amount of free or non-dissolved gas in a liquid, which will be hereinafter referred to as free gas.

The invention is also directed to the measurements relating to pulp consistency by means of density measurements, and toward an improved method and apparatus for use in on-line monitoring the amount of free gas in pulp stocks. By "on-line monitoring" throughout the disclosure and claims is meant, a method to be used while operating a process for immediate response to said process.

BACKGROUND OF THE INVENTION

Gases, in particular air are entrained in the pulp stock during the manufacture of paper. Entrained air or gases adversely affect the drainage of water from the pulp in the wet end of the paper machine. It is therefore, important to be able to accurately measure the amount of free gas in pulp stock at various stages of paper manufacture so as to be able to determine where in the system free gas enters the stock. Corrective measures can then be taken at appropriate places to minimize the amount of free gas entering the stock. The determination of the free gas content in a pulp also facilitates the measurement of the consistency by using a density measurement which is corrected for the free gas content in pulp.

The amount of air or gases in the stock can be measured by: measuring the density of the stock, removing all the gas from the stock, and measuring the volume removed; or by measuring the volume expansion of a stock sample by the reduction of pressure. Measuring the density of the stock to determine its free gas content is not very accurate. Removing all the free gas from a stock sample is time consuming and requires expensive equipment. The last method is the method commonly employed today. A known volume of a stock sample is subjected to a reduced pressure and the volume expansion of the sample is measured. One method of obtaining the reduced pressure is by using an electrically operated vacuum pump. Another method, developed at the Norwegian Pulp and Paper Institute, employs a pipette to hold a sample of pulp. A syringe burette is located below the pipette. Means are provided to connect the burette with the stock filled pipette, and a weighted piston in the burette is released for a short time to fall and create a pressure drop in the pipette. The distance the piston falls gives a measure of the air in the sample.

The known devices used to measure the amount of free gas in pulp stock, by measuring the volume expansion of a stock sample when the pressure is reduced, have disadvantages: The device employing a vacuum pump is cumbersome and requires careful control. The Norwegian Pulp and Paper Institute device has disadvantages affecting its accuracy. The loaded or weighted piston, used to create a pressure reduction in the stock has relatively high friction losses, and the volume measurement is not accurate, as the piston will tend to keep moving downward, as dissolved gases come out of solution. In addition, leakage occurs between the piston and adjacent walls leading to further inaccuracies.

BRIEF DESCRIPTION OF THE INVENTION

It is the purpose of the present invention to provide an improved apparatus, and a method of operating the apparatus, which can be used in simply, quickly and accurately measuring the amount of free gas in a sample of liquid.

In accordance with the present invention, the method used in measuring the amount of free gas in a liquid sample comprises: (a) filling a closed space defining a first volume with a sample of the liquid, measuring the density of the liquid sample in the closed space a first time, and (b) while holding the liquid in the space, enlarging the closed space to a predetermined reduced pressure and thereby to a second immediate larger volume and determining the density of said second immediate larger volume.

The density of said second larger volume may be obtained by immediately maintaining said second larger volume constant and later determining the density of the liquid sample or by determining, at once, the density of said second larger volume. The two density measurements, along with the pressures can then be used to calculate the amount of free gas in the stock, and also its consistency, if desired.

By the expression "determining the density of said second immediate larger volume", throughout the disclosure and claims is meant that such determination must be made as soon as the second immediate larger volume is reached in order to avoid the dissolved gas from coming out of solution when the volume is not fixed, or immediately fixing the volume. This is generally accomplished inter alia by either quickly fixing the second volume at a predetermined period of time and later measuring the density, or by quickly registering the density, as soon as said second volume is reached, to avoid the dissolved gas from coming out of solution The apparatus employed to carry out the method includes: liquid holding means defining a first volume at a given pressure, means for increasing said first volume of the liquid holding means to a second volume having a predetermined pressure for subjecting a liquid in said holding means to a known reduced pressure, and means for measuring the density of the liquid held at said first and said second volume.

In order to operate on-line, the apparatus is conveniently provided with means for the on-line transfer of a liquid, containing gas to be measured, to said holding means.

The liquid holding means has a container defining a chamber with an open end. A flexible wall fixed to the container closes the end of the chamber. Means are provided to position the wall in a first raised position in the chamber when defining the first known volume for the liquid holding means. A weight is freely suspended from the wall to create a predetermined force for a short predetermined period of time and moves the wall downwardly when the positioning means is released to enlarge the liquid holding means and subject the held liquid to a predetermined reduced pressure. The liquid holding means generally cooperates in time relationship with a means for quickly measuring the density.

The method provides a quick easy way for use in measuring the free gas content of a liquid. The density of the liquid before and after the expansion of the holding means can be quickly determined. No separate measure of the volume increase of the liquid holding means need be made, thus avoiding any difficulty or possibly inaccurate measurements. With the flexible wall, the apparatus employed eliminates any leakage of the liquid sample. In addition, the free suspension of the weight minimizes friction losses during operation. Furthermore, the apparatus is designed to minimize the entrapment of air in the apparatus which could also lead to inaccuracies.

The method is particularly useful in that it permits the consistency of a pulp stock to be determined without having to remove free gas from the pulp stock. Previously, it has been a requirement to remove as much free gas as possible from the stock before measuring its consistency in order to obtain accurate measurements. The present method allows for the determination of the free gas content which can be used as a correction for determination of consistency by means of a density measurement. Removal of the free gas is not necessary.

DESCRIPTION OF THE DRAWINGS

The invention will now be described in detail having reference to the accompanying drawings in which.

DESCRIPTION OF THE PREFERRED EMBODIMENTS

Figure 1:
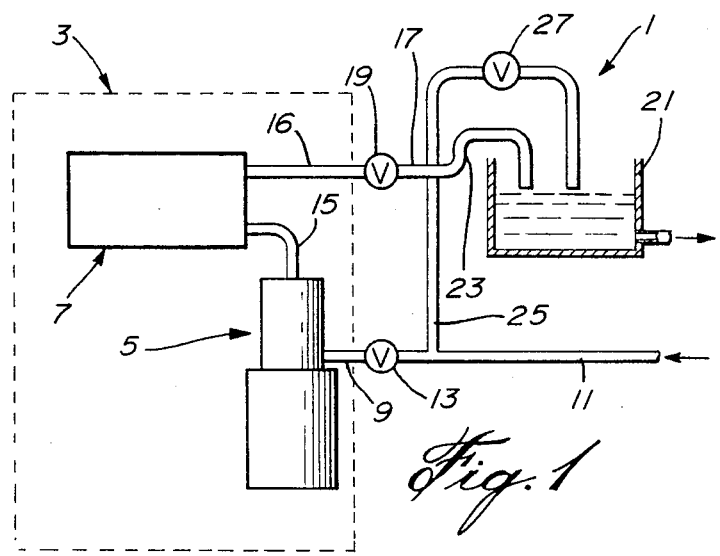
FIG. 1 is a schematic view of the apparatus employed to measure the undissolved or free gas content of a liquid.

The apparatus 1, as shown in FIG. 1, for use in measuring the free gas content of a liquid such as pulp stock includes means for holding a first volume of pulp liquid. The liquid holding means 3, enclosed in the dash lines of FIG. 1, includes a liquid holding chamber 5 and a device 7 for density measurement of the liquid. The density measuring device 7 may be for instance, a vibrating U-tube such as a "Dynatrol" TM gauge manufactured by Automatic Products, Houston, Tex. The inlet line 9 of the liquid holding means 3 is connected to a supply line 11 by a first valve 13 such as an air-operated ball valve. The inlet line 9 leads to a liquid holding chamber 5 which acts as a predetermined pressure reducing device and simultaneously a volume increasing means. An outlet line 15 from the liquid holding chamber 5 leads to the density measuring device 7. The outlet line 16 from the density measuring device 7 leads to a return line 17 via a second valve 19, similar to the first valve 13. The return line 17 returns the liquid to a tank 21. From tank 21, the liquid may be returned to its supply source. The return line 17 can be raised slightly as shown at 23 to provide a constant static back pressure in the return line 17 and the outlet line 16. A bypass line 25 is included, leading from the supply line 11 to the tank 21. A flow control valve 27 may be conveniently provided in the bypass line 25.

Figures 2, 3:
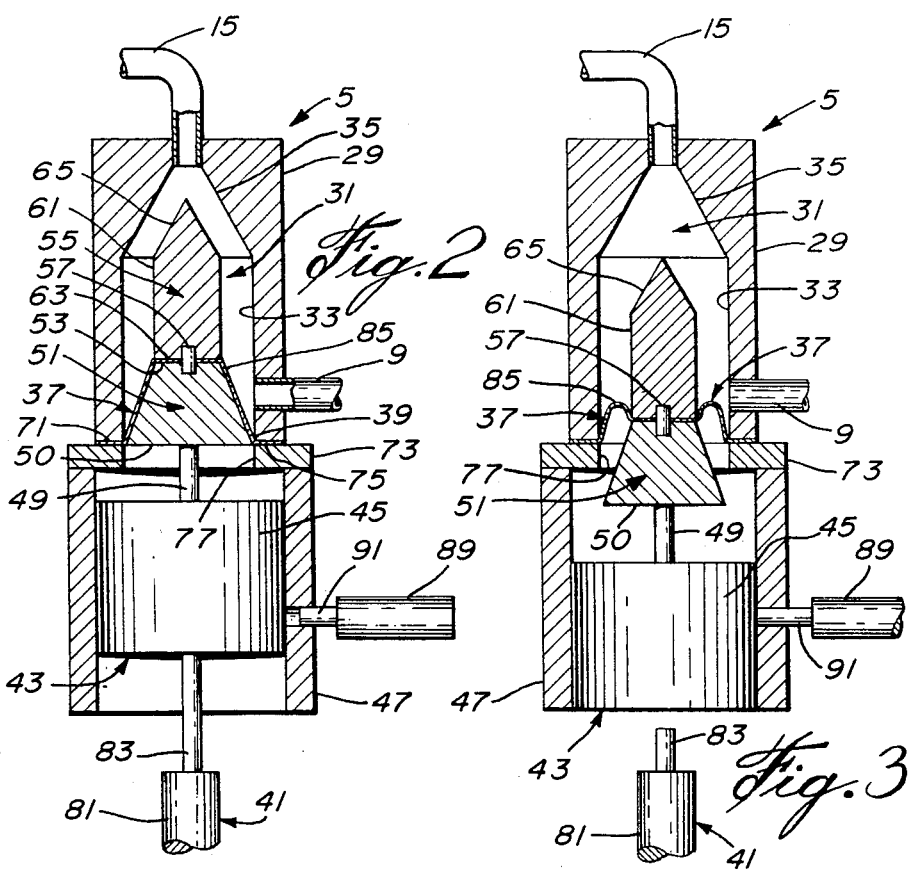
FIG. 2 is a detail cross-section view of the chamber for containing liquid in a first position used in the apparatus.
FIG. 3 is a detail cross-section view of the chamber but in the position having increased volume.

Referring now to FIG. 2, the liquid holding chamber 5 of the liquid holding means 3 has a container 29 defining a chamber 31 for holding liquid shown in FIGS. 2 and 3. The chamber 31 is defined by a cylindrical wall 33, with its longitudinal axis in a vertical position, and a truncated conical wall 35 at its upper end. A movable, flexible wall 37 closes the open lower end 39 of the chamber 31 as will be described. The inlet line 9 opens into the bottom portion of chamber 31 through cylindrical wall 33 and tangentially with respect to said cylindrical wall 33, whereby the entering liquid forms a vortex due to the centrifugal reaction exerted on said liquid by the cylindrical wall 33. The outlet line 15 connects with the upper end of the conical wall 35 leading axially from chamber 31.

The movable wall 37 is fixed to the container 29 and is located within the bottom portion of the chamber 31. The wall 37 is sized to have an area within the chamber that is greater than the cross-sectional area of the chamber so that it may move within the chamber 31. Means 41 are provided for positioning the wall 37 in a first raised position within the chamber 31 as will be described.

Means 43 are also provided for moving the wall 37 downwardly from its first raised position as shown in FIG. 2, to a lower position in the chamber as shown in FIG. 3, so as to reduce the pressure on liquid held in the liquid holding means 3. The wall moving means 43 comprises a weight 45 suspended from the wall 37. To minimize friction losses, the weight 45 is freely slidable in a vertical tubular guide 47 fastened to the bottom of the container 29 as will be described. A stem 49 extends up from the top center of the weight 45. The stem 49 is fixed to the lower end 50 of a bottom wall support 51. The wall 37 rests on the top end 53 of the bottom wall support 51. A top wall support 55 rests on top of the wall 37 and is joined to the bottom wall support 51 by suitable fastener means 57 passing through the center of the flexible wall 37. The bottom wall support 51 has a truncated conical shape and is sized to fit up into the chamber 31 from the open bottom end of the chamber. The lower end 50 of the bottom wall support 51 has a diameter just slightly smaller than the diameter of chamber 31. The top end 53 of bottom wall support 51 is smaller in diameter than its lower end 50. The top wall support 55 has a cylindrical section 61 axially located within chamber 31. The circular bottom end 63 of the section 61 covers the top end 53 of the bottom wall support 51. A conical section 65 extends up from the top of the cylindrical section 61 into the conical section 35 of chamber 31.

The container 29 is fixed at its bottom end 71 to a cover plate 73 on the tubular guide 47 by suitable fastening means. The outer peripheral portion 75 of the flexible wall 37 is fixed between the bottom end 71 of stock holding chamber 5, and cover plate 73 on the turbular guide 47. A central opening 77 is provided in the cover plate 73 through which stem 49 and bottom wall support 51 can move.

The means 41, provided for positioning the flexible wall 37 in a first raised position within chamber 31, as shown in FIG. 2, comprise a first air cylinder 81 positioned beneath the weight 45. The first air cylinder 81 extends axially and supports the weight 45 and is mounted by suitable means (not shown) to the guide 47. The stem 83 of the air cylinder 81 is extended to raise weight 45 and thus the attached wall supports 51, 55 to place the flexible wall 37 in the first raised position. In this first raised position, the bottom wall support 51 just fits within the chamber 31, and the flexible wall 37 has a truncated conical shape within the chamber 31, as shown in FIG. 2. When the stem 83 of cylinder 81 is retracted, as shown in FIG. 3, the weight 45 falls freely in guide 47 pulling wall supports 51, 55 with it, and the attached wall 37. The sides 85 of the wall 37 roll downwardly, as shown in FIG. 3, as the bottom wall support 51 moves out of the chamber 31.

Means are provided to stop the free fall of the weight 45, and thus the downward movement of the wall 37 after a short predetermined period of time, for instance one half a second. The stopping means comprises a second air cylinder 89 mounted on guide 47 and extending transverse to the direction of movement of weight 45. Actuation of cylinder 89 causes its stem 91 to move inwardly contacting weight 45 and halting its downward movement. This halts the downward movement of wall 37.

METHOD

During use of the apparatus, the first air cylinder 81 has its stem 83 extended to locate the wall 37 of the chamber 31 in its first raised position, the liquid holding means 3 has a first volume. The second air cylinder 89 has its stem 91 retracted. The valves 13, 19 in the inlet and outlet lines 9, 15 respectively, are opened allowing the liquid to flow through the liquid holding means 3 including the holding chamber 5 and the density measuring device 7. The liquid flows into and through chamber 31 of the stock holding chamber 5 and forms a vortex to ensure that free gas is removed from the walls of the chamber 31 and that substantially no free gas can collect in any part of the assembly. The bypass line 25 can also be opened at this time, via control valve 27, allowing any large gas bubbles in the liquid to pass directly to the tank 21. Once the liquid holding means 3 including the chamber 31, has been flushed through with the liquid and filled, valve 13 is closed after which valve 19 is closed, thereby ensuring that atmospheric pressure exists throughout the liquid holding means 3. The density of the liquid in the filled liquid holding means 3 is now measured by the density gauge 7. After the density has been measured, the stem 83 of air cylinder 81 is retracted allowing weight 45 to fall freely, moving the flexible wall 37 downwardly and reducing the pressure in the liquid holding means while increasing its volume. After a short predetermined period of time, the second air cylinder 89 is actuated to extend its stem 91 and stop movement of weight 45 thus "freezing" the volume of the liquid holding chamber 5 and thereby of the liquid holding means 3 at its new second immediate larger volume to prevent any further volume increase due to dissolved gases from coming out of solution. The density of the liquid in the enlarged liquid holding means 3 is now measured by the density gauge 7.

Instead of freezing the volume of the holding chamber and carrying out density measurements on the constant second immediate larger volume, one way to determine free gas content involves electronically sampling the analogue signal output of the density measurement device to obtain a series of density measurements, over a predetermined period of time, while the flexible wall is falling freely with the weight. The function, density versus time, is calculated to determine the onset of dissolved gas coming out of solution and contributing to volume expansion. Initially, the function is a substantially straight line reflecting free gas expansion in the liquid, A transition then occurs as the function becomes non-linear reflecting the onset of dissolved gasses coming out of solution and contributing to the volume expansion. The density corresponding to this transition is then selected to be used in the following calculation.

With the initial volume of liquid subjected to atmospheric pressure and the second immediate larger volume produced by a pressure which is one half of atmospheric pressure, the free gas content of the liquid sample can be calculated from the expression:

$$Va/V_1 = (1/d_2)(d_1 - d_2)$$

where
- $Va$ = volume of air in the stock sample
- $V_1$ = volume of the stock holding means
- $d_1$ = density of the stock sample in the stock holding means at its first volume
- $d_2$ = density of the stock sample in the stock holding means at its enlarged volume With the free gas content determined from the above equation, the density of the liquid sample can be corrected to give the density of the liquid sample with all free gas removed, thereby enabling consistency to be determined as is known by those skilled in the art.

Instead of using a weight suspended from the wall to create a predetermined force, other means may be used, as is well known in the art, such as a solenoid arrangement, pneumatic devices, and other mechanical equivalents, to actuate the movable wall 37.

If one wishes, the movable wall 37 may be repeatedly moved for increasing time periods in order to additionally determine the amount of dissolved gas in a sample.

The method and apparatus described hereinabove can be used to measure properties of other liquids comprising solid, liquid and gas mixtures such as liquids employed in ore processing, or in the manufacture of liquid gel or emulsion based explosives.

Having described the invention, modifications will be evident to those skilled in the art without departing from the spirit of the invention as defined in the appended claims.

I claim:

1. A method for use in determining the amount of non-dissolved free gas in a liquid sample, comprising the steps of: (a) filling a closed expandable space defining a first volume with a sample of the liquid, measuring the density of the liquid sample in the closed space a first time, and (b) while holding the liquid in said closed expandable space, reducing the pressure of the liquid sample to a predetermined reduced pressure and thereby enlarging said closed expandable space to a second immediate larger volume to expand the non-dissolved free gas in said liquid sample, the amount of said non-dissolved free gas determining the size of said second immediate volume, while maintaining dissolved gas in solution, and determining the density of said second immediate larger volume, the function density versus time, under said immediate larger volume, being substantially a straight line reflecting the non-dissolved free gas expansion in the liquid.

2. The method as defined in claim 1 wherein once the second immediate volume is reached, the density is immediately measured.

3. A method as defined in claim 1 wherein said space is confined within a plurality of walls, at least one of said walls being outwardly movable and wherein said movable wall is displaced by applying an outwardly directed predetermined force.

4. A method as defined in claim 3 wherein said movable wall is releasably held a short predetermined period of time after its displacement from said first volume to said second immediate larger volume.

5. A method as defined in claim 3 wherein the wall is vertically movable and said force is a weight suspended from the wall.

6. A method as defined in claim 3 wherein the step of moving the wall is repeated for increasing time periods, in order to additionally determine the amount of dissolved gas in the sample.

7. A method as defined in claim 1 for use in determining directly the amount of non-dissolved free gas in a liquid sample where in step (b), the predetermined force is one half the original pressure of step (a), and the gas content of the liquid can be obtained by the expression:

$$Va/v_1 = (1/d_2)(d_1 - d_2)$$

where
$Va$ = volume of air in the stock sample
$V_1$ = volume of air in the closed expandable space of step (a)
$d_1$ = density of the sample of liquid in step (a)
$d_2$ = density of the sample of liquid in step (b).

8. The method as defined in claim 1 wherein prior to filling said closed space, said space is flushed with an amount of liquid sample forming a vortex to wet said space, thereby removing entrapped gas in said space and ensure that substantially no free gas collects in any part of said space.

9. The method as defined in claim 1 wherein the density of liquid is simultaneously determined, as the second volume is reached.

10. The method as defined in claim 1 wherein the density of the liquid is continuously determined from said first volume to said second volume.

11. The method as defined in claim 1 wherein the liquid sample is a wood pulp stock.

12. An apparatus, for use in measuring the amount of non-dissolved free gas in a liquid sample, comprising an expandable liquid holding means defining a first volume at a given pressure for holding a liquid sample containing gas, means for quickly expanding said first volume of the liquid holding means to a second variable volume under a predetermined reduced pressure, for quickly subjecting said liquid containing gas in said holding means to a known reduced pressure to expand the non-dissolved free gas in said liquid containing gas, and means for measuring the density of the liquid held at said first, and for measuring in time relation to said second volume the density of said second volume, said apparatus producing a function of the density versus time which is a straight line reflecting the non-dissolved free gas expansion in the liquid.

13. The apparatus as defined in claim 12 which further includes means for the on-line transferring of a liquid, containing gas to be measured, to said liquid holding means.

14. An apparatus as defined in claim 12 wherein the liquid holding means is a container defining a chamber with an open end, and a flexible wall slidable within the container to close said end of the chamber, said flexible wall having an area within the chamber which is larger than the cross-section area of the chamber.

15. An apparatus as defined in claim 14 including means for positioning the flexible wall in a first raised position within the chamber, when defining the first volume of the liquid holding means, and wherein the means for increasing the volume of the liquid holding means comprises means for quickly moving the flexible wall downwardly from a first raised position within the chamber.

16. An apparatus as defined in claim 15 wherein the means for moving the flexible wall downwardly comprises a weight suspended from the wall to reduce the pressure of said second variable volume to half the original pressure of the liquid sample in said first volume and thereby obtaining the volume of air in the stock sample by the formula:

$$Va/V_1 = (1/d_2)(d_1 - d_2)$$

where
$Va$ = volume of air in the liquid sample containing gas
$V_1$ = first volume of stock holding means
$d_1$ = density of the stock sample in the stock holding means at its first volume
$d_2$ = density of the stock sample in the stock holding means at its second variable volume.

17. An apparatus as defined in claim 16 wherein the means for moving the wall downwardly includes means for stopping downward movement of the wall after a predetermined period of time.

18. An apparatus as defined in claim 12 wherein said transfer means consists in a first passageway for delivering into said liquid holding means, said liquid containing gas, and a second passageway for removing said liquid containing gas and wherein said passageways are positioned to produce into said liquid a vortex of said liquid containing gas to ensure that substantially no free gas collects in said liquid holding means.

* * * * *